(12) United States Patent
Miya et al.

(10) Patent No.: US 7,147,748 B2
(45) Date of Patent: Dec. 12, 2006

(54) PLASMA PROCESSING METHOD

(75) Inventors: Go Miya, Ibaraki (JP); Hiroyuki Kitsunai, Ibaraki (JP); Junichi Tanaka, Tsuchiura (JP); Toshio Masuda, Toride (JP); Hideyuki Yamamoto, Kudamatsu (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/779,742

(22) Filed: Feb. 18, 2004

(65) Prior Publication Data
US 2004/0166598 A1    Aug. 26, 2004

Related U.S. Application Data

(62) Division of application No. 10/377,826, filed on Mar. 4, 2003.

(51) Int. Cl.
*H01L 21/00* (2006.01)
*C23C 16/00* (2006.01)

(52) U.S. Cl. .................... 156/345.25; 156/345.24; 118/712; 204/192.33; 204/298.03; 204/298.32; 216/67

(58) Field of Classification Search .............. 438/7, 438/8, 9, 710; 216/59, 60, 67; 156/345.24, 156/345.25; 118/712; 204/192.33, 298.03, 204/298.32
See application file for complete search history.

(56) References Cited

U.S. PATENT DOCUMENTS

| | | | | |
|---|---|---|---|---|
| 5,683,538 A | * | 11/1997 | O'Neill et al. | 156/345.28 |
| 5,711,843 A | * | 1/1998 | Jahns | 156/345.24 |
| 6,090,302 A | * | 7/2000 | Smith et al. | 216/60 |
| 6,153,115 A | * | 11/2000 | Le et al. | 216/60 |
| 6,521,080 B1 | * | 2/2003 | Balasubramhanya et al. | 156/345.24 |
| 6,716,300 B1 | * | 4/2004 | Kaji et al. | 156/345.24 |
| 6,825,920 B1 | * | 11/2004 | Lam et al. | 356/72 |

FOREIGN PATENT DOCUMENTS

| JP | 2000-331985 | 11/2000 |
|---|---|---|
| JP | 2002-018274 | 1/2002 |

* cited by examiner

*Primary Examiner*—Ram N. Kackar
(74) *Attorney, Agent, or Firm*—Antonelli, Terry, Stout and Kraus, LLP.

(57) ABSTRACT

A plasma processing method using a plasma processing apparatus having a process chamber in which a substrate is subjected to a plasma processing, a light-receiving part, a spectrometer unit, an arithmetic unit, a database, a determination unit for determining that an end point of seasoning is reached as a condition of the process chamber, and an apparatus controller. The method includes the steps of converting a multi-channel signal output from the spectrometer unit into a batch of output signals, finding differences between the output signals and output signals of a preceding batch, determining the average value of the differences in one batch, the difference between the maximum and the minimum of the differences in one batch and the standard deviation of the differences in one batch, and comparing the determined values with a preset threshold.

12 Claims, 14 Drawing Sheets

FIG. 7
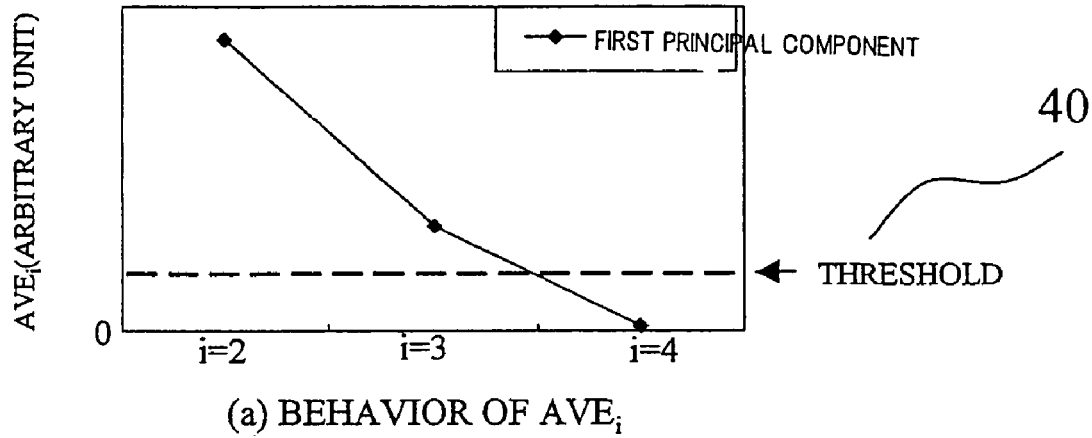
(a) BEHAVIOR OF $AVE_i$
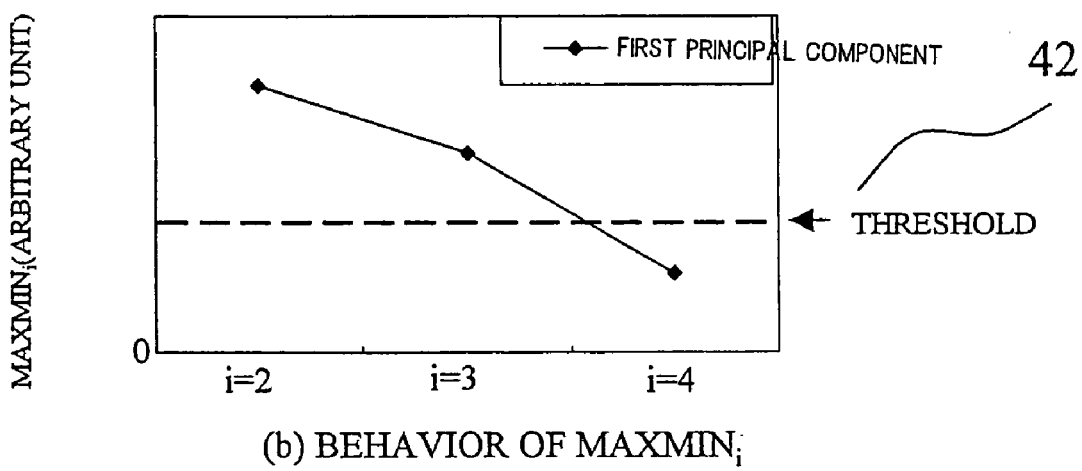
(b) BEHAVIOR OF $MAXMIN_i$
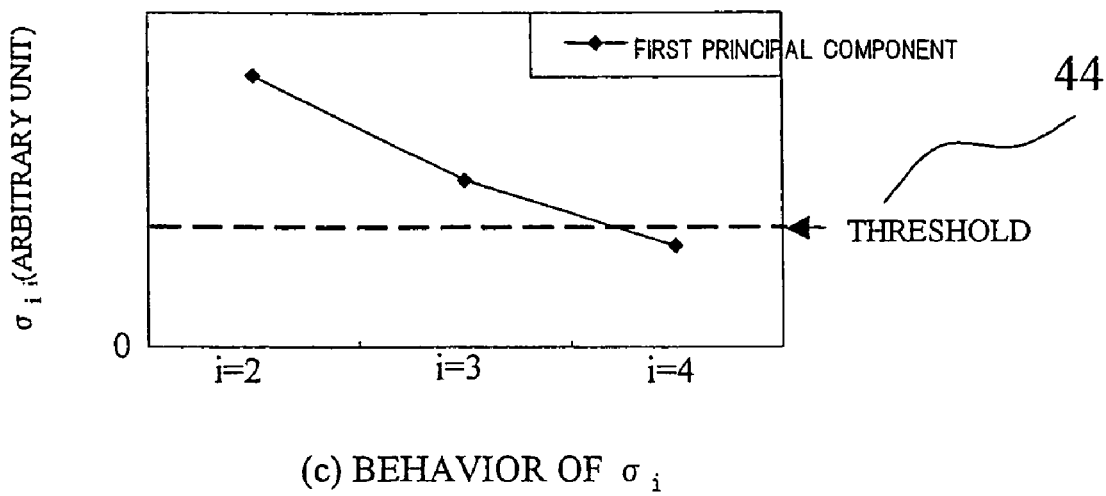
(c) BEHAVIOR OF $\sigma_i$

FIG. 8
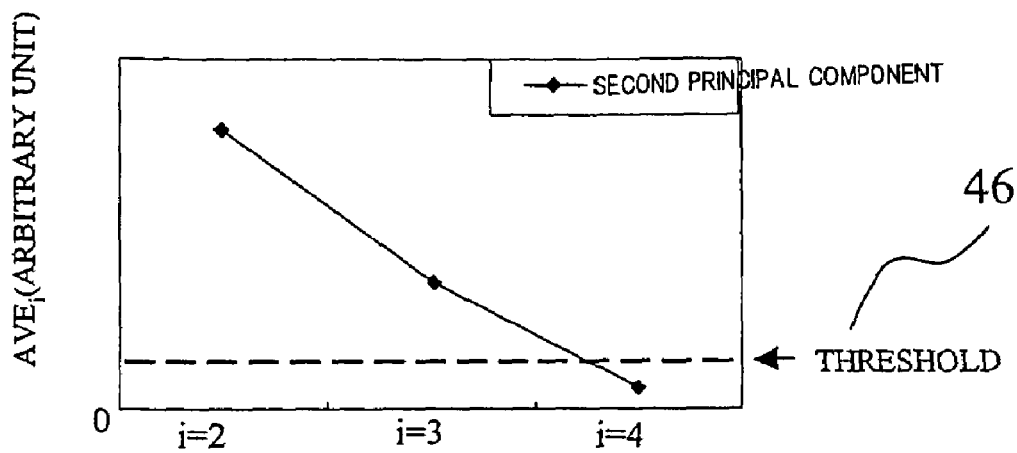
(a) BEHAVIOR OF $AVE_i$
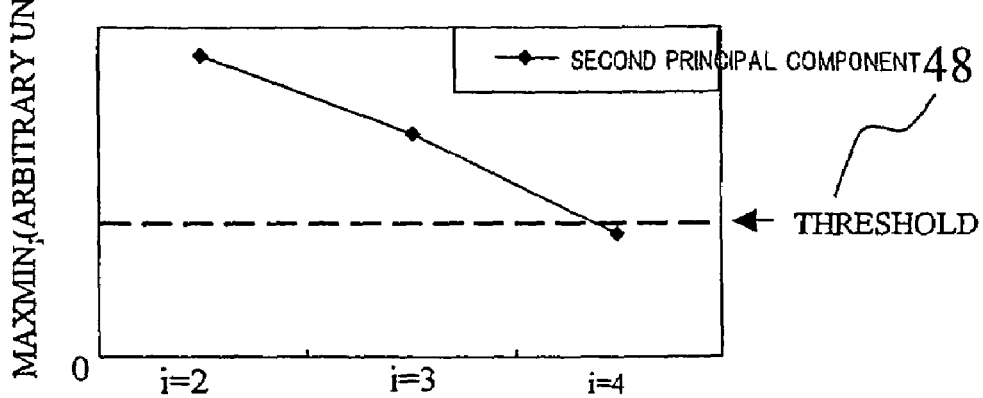
(b) BEHAVIOR OF $MAXMIN_i$
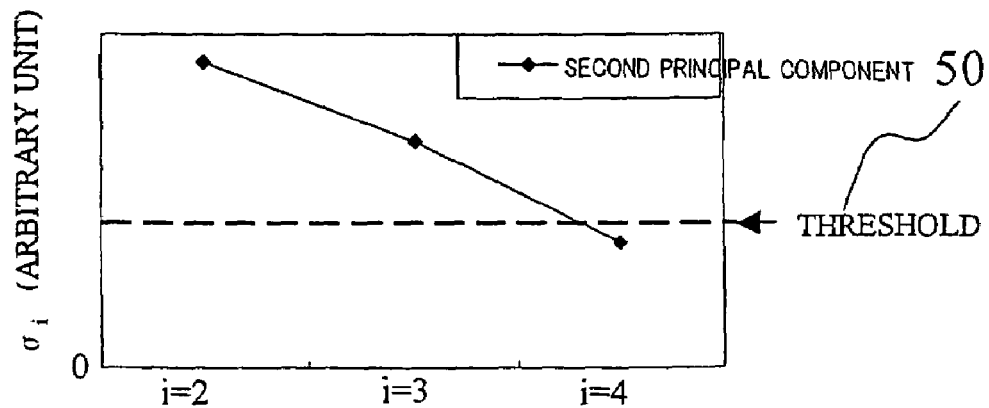
(c) BEHAVIOR OF $\sigma_i$

FIG. 11

| | | INADEQUATE SEASONING | | ADEQUATE SEASONING |
|---|---|---|---|---|
| | | i=2 | i=3 | i=4 |
| FIRST PRINCIPAL COMPONENT | $AVE_i$ | 0 | 1 | 2 |
| | $MAXMIN_i$ | 0 | 0 | 2 |
| | $\sigma_i$ | 0 | 0 | 2 |
| SECOND PRINCIPAL COMPONENT | $AVE_i$ | 0 | 1 | 2 |
| | $MAXMIN_i$ | 1 | 1 | 2 |
| | $\sigma_i$ | 0 | 0 | 2 |
| THIRD PRINCIPAL COMPONENT | $AVE_i$ | 0 | 0 | 1 |
| | $MAXMIN_i$ | 0 | 1 | 2 |
| | $\sigma_i$ | 0 | 0 | 2 |
| TOTAL POINT | | 1 | 4 | 17 |
| | | 60 | 61 | 62 |

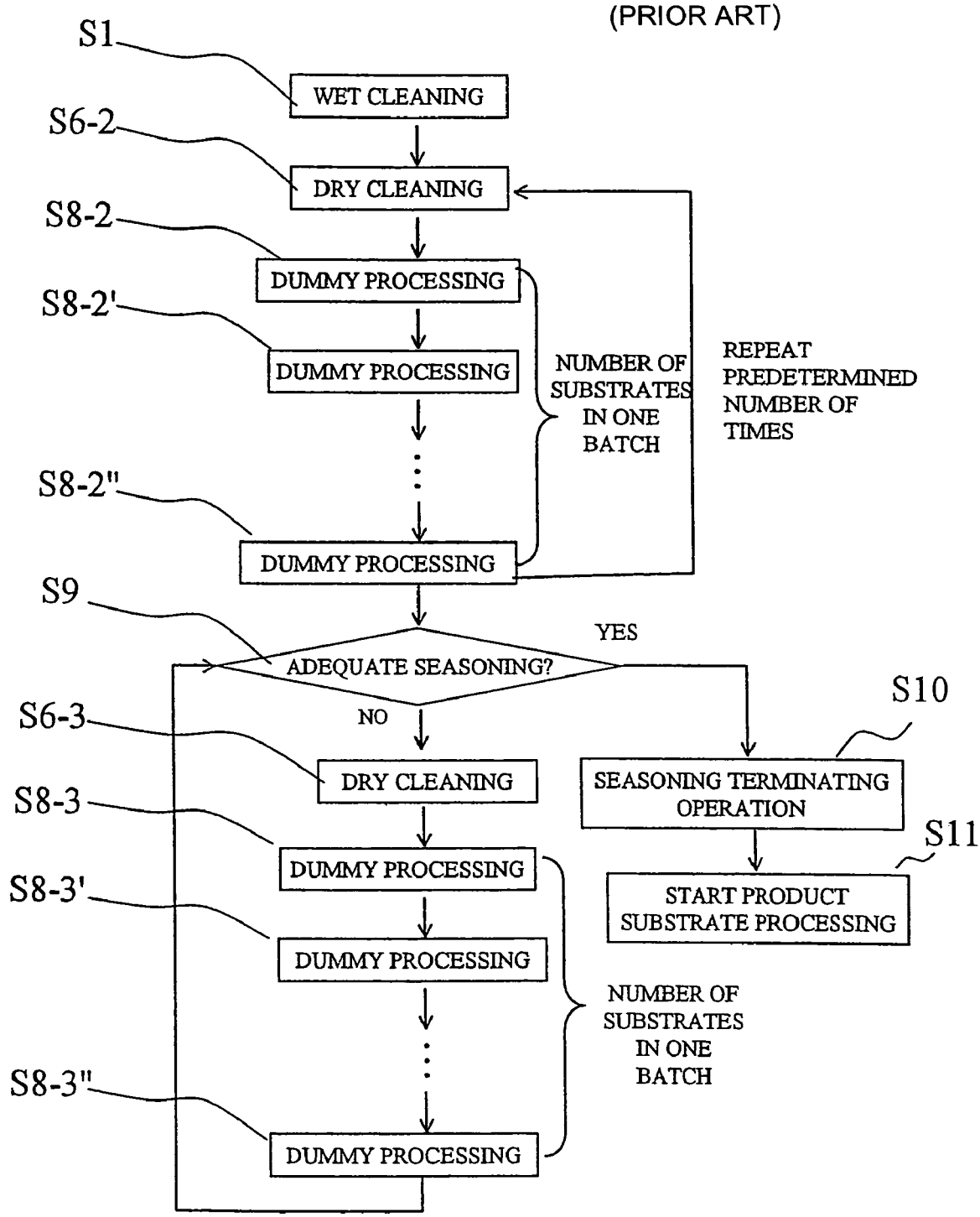

PLASMA PROCESSING METHOD

CROSS REFERENCE TO RELATED APPLICATION

This is a divisional of U.S. application Ser. No. 10/377,826, filed Mar. 4, 2003, the subject matter of which is incorporated by reference herein.

FIELD OF THE INVENTION

The present invention relates to a plasma processing apparatus for processing a semiconductor substrate, such as a semiconductor wafer, or a LCD substrate, and a plasma processing method implemented by the plasma processing apparatus.

DESCRIPTION OF THE RELATED ART

Conventionally, in processes for manufacturing a semiconductor substrate, such as a semiconductor wafer, or a LCD (liquid crystal display) substrate, plasma processing apparatuses such as a plasma etching apparatus involving a reactive plasma and a plasma CVD (chemical vapor deposition) apparatus have been used.

These plasma processing apparatus have a process chamber for housing an object to be processed, such as a semiconductor substrate, and a non-volatile reaction byproduct produced during plasma-processing of the object to be processed is deposited on the inner walls of the process chamber. In the subsequent processing, the deposit may fall off from the inner wall of the process chamber in the form of particles, which may fall onto a surface of the object to be processed and adhere thereto. The particles adhering to the surface of the object to be processed causes short-circuit or disconnection in a wiring in an integrated circuit provided thereon, or causes insufficient etching. This results in a failure in a semiconductor device, and thus, the manufacturing yield of the semiconductor device decreases.

To avoid this, during manufacture of a semiconductor or LCD, a processing referred to as dry cleaning such as gas cleaning involving a reactive gas and plasma cleaning involving a reactive plasma is regularly carried out to remove the reaction byproduct deposited on the inner wall of the process chamber without bringing the pressure in the process chamber to the level of atmospheric pressure, so that the inside of the process chamber is kept clean.

Now, referring to FIG. 13, a plasma etching processing for a semiconductor substrate in the case of mass production will be described.

First, a process chamber of a semiconductor processing apparatus is dry-cleaned (step S6). This allows a reaction byproduct deposited on the inner wall of the process chamber to be removed. In many cases, this dry cleaning S6 is carried out using a substrate different from the product substrate, referred to as a dummy substrate, being installed in the process chamber. However, the dummy substrate is not necessarily installed in the process chamber.

Then, a processing referred to as aging is carried out (step S7). Generally, the dry cleaning S6 utilizes a gas that is different from the process gas used in the plasma etching processing. Therefore, another reaction byproduct results due to the dry cleaning S6 and remains on the inner wall of the process chamber, thereby changing the condition in the process chamber. Thus, this aging processing is carried out under a condition exactly or nearly the same as that of a common plasma etching processing to make the condition in the process chamber adequate. In many cases, this aging S7 is carried out with the dummy substrate being installed in the process chamber. However, the dummy substrate is not necessarily installed in the process chamber.

After the aging S7, if the dummy substrate is in the process chamber, it is removed from the process chamber. Then, the product substrate is installed into the process chamber and subjected to plasma etching (step S8). Upon completion of the product substrate processing S8, the product substrate is removed from the process chamber, and another product substrate is installed into the process chamber and subjected to the same processing (step S8'). This substrate processing is performed on a batch of substrates (steps S8 to S8").

The plasma etching of the semiconductor substrates is carried out by repeating the dry cleaning S6, the aging S7 and the product substrate processings S8 to S8".

The number of substrates successively processed will be explained. In general, a plurality of semiconductor substrates are packed into a cassette for handling. The batch of the plurality of substrates packed into one cassette is sometimes called "lot". The number of the semiconductor substrates in one lot is 25 if the semiconductor substrates have a diameter of 200 mm, or 13 if the substrates have a diameter of 300 mm. Therefore, the number of the substrates processed in a batch described above is often equal to the number of the semiconductor substrates in one lot. However, the number of the semiconductor substrates in one lot may be different from the number of the substrates subjected to the product substrate processings S8 to S8" in a batch. Furthermore, in the case where a plurality of products are processed in one plasma processing apparatus, the number of the product substrates subjected to the product substrate processings S8 to S8" in a batch may vary from one product to another.

In the process described above, no dry cleaning is carried out after each of the product substrate processings S8 to S8". However, a dry cleaning that takes less time than the dry cleaning S6, which is a short dry cleaning performed after each etching, may be carried out after each of the product substrate processings S8 to S8".

As described so far, the reaction byproduct resulting due to the product substrate processings S8 to S8" and deposited on the inner walls of the process chamber is removed by the dry cleaning S6. However, any deposit that cannot be removed by the dry cleaning S6 is removed after releasing the process chamber to the atmosphere by an operation referred to as wet cleaning or manual cleaning, in which the operator cleans the inner walls of the process chamber manually by means of water, alcohol or the like.

Since a reactive plasma is used in the plasma processing apparatus as described above, components in the process chamber maybe chemically or thermally damaged or worn, and therefore, they require periodic replacement. A component which is at the end of a predetermined life span thereof is replaced with a new one when the wet cleaning is carried out.

The condition of the inner wall of the process chamber immediately after the wet cleaning is different from the stable condition during mass production. Therefore, the plasma etching apparatus has a problem in that the performances thereof vary, including the etch rate, the etch rate distribution in the surface of the semiconductor substrate, the etching selectivity between an object to be etched and a mask or base, that is, the ratio of etch rate therebetween, and the resulting shape of the etched object. Similarly, the plasma CVD apparatus has a problem in that the performances thereof vary, including the film deposition rate, the film deposition rate distribution in the surface of the semiconductor substrate and the quality of the deposited film.

In order to avoid the problem, in mass production of semiconductor or LCD, a processing referred to as seasoning is commonly carried out, thereby bringing the condition in the process chamber which has been changed by the wet cleaning close to the stable condition during mass production. The seasoning is often carried out by simulating the semiconductor substrate processing shown in FIG. 13.

Here, referring to FIG. 14, exemplary wet cleaning and seasoning performed on the plasma etching apparatus for processing semiconductor substrates will be described. The seasoning process comprises a dry cleaning processing, a dummy substrate processing (semiconductor substrate different from the product substrate) and a confirmation processing for confirming whether an adequate (sufficient) seasoning is performed or not.

First, the plasma process chamber of the plasma processing apparatus is wet-cleaned (step S1).

Then, the process chamber is evacuated to a predetermined degree of vacuum, before dry cleaning is carried out (step S6-2). The dry cleaning S6-2 removes any organic solvent or the like remaining on the inner walls of the process chamber after the wet cleaning.

Then, an etching processing using a dummy substrate which simulates the actual processing (referred to as dummy processing hereinafter) is carried out (step S8-2). After the dummy processing S8-2 is completed, the dummy substrate is removed from the process chamber, another dummy substrate is installed in the process chamber, and the same dummy processing as step S8-2 is carried out (step S8-2'). The dummy processing is carried out on a batch of substrates (for example, 25 substrates) (step S8-2").

After the dummy processings S8-2 to S8-2" are completed, dry cleaning is carried out (step S6-2). By the dry cleaning S6-2, any reaction byproduct deposited on the inner wall of the process chamber during the dummy processings is changed into a volatile compound and removed from the process chamber. These processings, that is, the dry cleaning S6-2 and the dummy processings S8-2 to S8-2" are repeated for a predetermined number of times.

After that, the confirmation processing for confirming whether an adequate seasoning is performed or not is carried out (step S9). For example, this processing involves etching a wafer having a surface coated with a film of a predetermined material (silicon dioxide ($SiO_2$), for example) and determining the average value or uniformity of the etch rates in the surface of the wafer. If the average value or uniformity of the etch rates in the surface of the wafer meets a predetermined criterion, the seasoning is determined to be adequate. If it does not meet the criterion, the seasoning is determined to be inadequate.

If the seasoning is determined to be adequate in the confirmation processing S9, a seasoning terminating operation is carried out (step S10), the product substrate processing is started (step S11) to start a plasma processing on the product substrate.

On the other hand, if the seasoning is determined to be inadequate in the confirmation processing S9, the same dry cleaning as that in the step S6-2 is further carried out (step S6-3). Then, the same dummy processings as those in the steps S8-2 to S8-2" are carried out on the batch of substrates (steps S8-3 to S8-3"). And then, the confirmation processing for determining whether an adequate seasoning is performed or not is carried out (step S9).

The processings S6-3 to S8-3" are repeated until the seasoning is determined to be adequate in the confirmation processing S9.

In the process described above, aging is not carried out after the dry cleaning steps S6-2 and S6-3. However, an aging similar to that in the step S7 in FIG. 13 may be carried out after the dry cleaning steps S6-2 and S6-3.

Furthermore, in the process described above, a dry cleaning is not carried out after the dummy processings S8-2 to S8-2' and S8-3 to S8-3". However, a dry cleaning that takes less time than the dry cleaning steps S6-2 and S6-3, which is a short dry cleaning performed after each etching, may be carried out after the dummy processings S8-2 to S8-2' and S8-3 to S8-3".

In the prior art described above, the number of substrates subjected to the dummy processing in the seasoning is determined empirically. For example, if the dummy processing in the seasoning is previously determined to be performed on five lots of substrates, the seasoning process comprising the dummy processings for five lots of substrates is carried out after the wet cleaning. And then, the operator performs the confirmation processing S9 to evaluate the processing performances including the film deposition rate, the etching rate or uniformity thereof in the surface, thereby determining whether an adequate seasoning is performed or not, that is, whether the condition in the process chamber after the wet cleaning has been brought close to the stable condition during mass production.

If the seasoning is inadequate, a predetermined performance cannot be attained in the product substrate processing, whereby the yield of mass production of the substrates is reduced. Thus, more dummy processings than the minimum number of those required is often allowed for in the seasoning. The excessive dummy processings are not desirable because it leads to reduction of throughput of the semiconductor manufacturing apparatus, and therefore, reduction of production efficiency. Recently, in accordance with the trend toward increasing the semiconductor substrate diameter, the cost of one dummy substrate is increased. Therefore, there has been an increasing demand to reduce the number of dummy substrates used in the dummy processings.

On the other hand, due to a variation in quality of the wet cleaning S1 or the like, the condition in the process chamber may not become close to the stable condition during mass production despite of a predetermined seasoning. In such a case, as shown in FIG. 14, the operator is required to repeatedly carry out the dry cleaning S6-3, the dummy processings S8-3 to S8-3" and the confirmation processing S9. Therefore, the process requires more time and work, and the production efficiency is reduced.

If it is possible to determine whether the seasoning is adequate or not during the seasoning so that minimum seasoning is carried out, the number of dummy substrates being used can be reduced to a minimum. Thus, there is a need for a method determining whether the seasoning provides a condition in the process chamber adequately close to the stable condition during mass production, that is, a method of determining the end point of the seasoning.

As a technique for determining the end point of the plasma processing of the product substrate, there has been proposed a technique in which a substrate same as the product substrate is processed in advance to perform a principal component analysis of the emission spectrum of the plasma, and then, the principal component analysis of the emission spectrum measured in the actual processing of the product substrate is performed to determine the end point of the processing based on a change in principal component score (refer to Patent Reference 1, for example). This technique is effective in detecting the endpoint of the processing of each single product substrate. However, according to this technique, the end point of the seasoning process which involves successive processings of a plurality of substrates cannot be detected.

Furthermore, as a technique for determining the endpoint of the seasoning, there has been proposed a technique in which the condition in the process chamber is detected by comparing reference principal component score and residual score calculated based on a principal component analysis performed on electrical data of a high-frequency power supply of the stabilized processing apparatus with principal component score and residual score calculated based on a principal component analysis performed on a plurality of pieces of electrical data obtained for any condition of the process chamber (see Patent Reference 2, for example). This technique is effective in detecting the condition in the process chamber which is changed by the seasoning after the wet cleaning. However, the wet cleaning is manually carried out and thus, the quality thereof varies significantly. As a result, the condition in the process chamber after the seasoning also varies significantly. In other words, various changes of the condition in the process chamber for various types of seasonings are less reproducible, and thus, comparing the reference principal component score and residual score with the principal component score and residual score for arbitrary seasoning may not provide an adequate precision of the detection of the end point of the seasoning.

[Patent Reference 1]
Japanese Patent Laid-Open No. 2000-331985
[Patent Reference 2]
Japanese Patent Laid-Open No. 2002-18274

SUMMARY OF THE INVENTION

An object of the invention is to provide a plasma processing apparatus and a plasma processing method which can determine with high precision an end point of a seasoning, that is, whether the seasoning is adequately performed or not based on data derived from plasma emission data obtained in the seasoning, which is performed immediately after a wet cleaning.

The object described above is attained by a plasma processing apparatus having a process chamber in which a substrate is processed, comprising: a light-receiving part for monitoring a plasma emission; a spectrometer unit for performing a spectrometry on the plasma emission; an arithmetic unit for performing an arithmetic operation on a signal obtained in the spectrometer unit to produce an output signal; a determination unit for making a determination using the output signal to produce an apparatus control signal; and an apparatus controller for controlling the plasma processing apparatus in response to the apparatus control signal from the determination unit, in which a plasma emission in a batch of plasma processings in a seasoning processing is monitored, a multivariate analysis is performed on the resulting plasma emission data, differences between output signals obtained by the multivariate analysis and output signals for the preceding batch of plasma processings are found, an average value of the differences in one batch, a difference between a maximum and a minimum of the differences in one batch and a standard deviation of the differences in one batch are determined, and the values are compared with a preset threshold.

The object described above is attained by the plasma processing apparatus and plasma processing method described above, in which for a plurality of output signals, differences between the output signals and output signals for the preceding batch of plasma processings are found, an average value of the differences in one batch, a difference between a maximum and a minimum of the differences in one batch and a standard deviation of the differences in one batch are determined, and the values are compared with a preset threshold.

The object described above is attained by the plasma processing apparatus and plasma processing method described above, in which for a plurality of output signals, differences between the output signals and output signals for the preceding batch of plasma processings is found, an average value of the differences in one batch, a difference between a maximum and a minimum of the differences in one batch and a standard deviation of the differences in one batch are determined, the values are compared with a plurality of preset thresholds to calculate a point for each of the values, and the sum of the points is compared with a preset threshold.

The object described above is attained by the plasma processing apparatus and plasma processing method described above, in which one or more output signals are calculated using one or more previously registered filter vectors, differences between the output signals and output signals for the preceding batch of plasma processings are found, and an average value of the differences in one batch, a difference between a maximum and a minimum of the differences in one batch and a standard deviation of the differences in one batch are compared with one or more preset thresholds.

The object described above is attained by the plasma processing apparatus and plasma processing method described above, in which evacuation of the process chamber, confirmation of the degree of vacuum, confirmation of an apparatus abnormality and the above-described processing method are automatically performed.

BRIEF DESCRIPTION OF THE DRAWINGS

FIG. 7(a) is a graph showing a behavior of a value $AVE_j$ calculated based on the output signal z (first principal component score, here) according to the first embodiment;

FIG. 7(b) is a graph showing a behavior of a value MAXMIN$_i$ calculated based on the output signal z (first principal component score, here) according to the first embodiment;

FIG. 7(c) is a graph showing a behavior of a value σ$_i$ calculated based on the output signal z (first principal component score, here) according to the first embodiment;

FIG. 8(a) is a graph showing a behavior of a value AVE$_i$ calculated based on the output signal z (second principal component score, here) according to a second embodiment;

FIG. 8(b) is a graph showing a behavior of a value MAXMIN$_i$ calculated based on the output signal z (second principal component score, here) according to the second embodiment;

FIG. 8(c) is a graph showing a behavior of a value σ$_i$ calculated based on the output signal z (second principal component score, here) according to the second embodiment;

FIG. 11 is a table used for determining whether the seasoning is adequate or not based on the points assigned to the values AVE$_i$, MAXMIN$_i$ and σ$_i$ calculated based on the output signals z (first, second and third principal component scores, here) according to the second embodiment;

FIG. 14 is a flowchart of a conventional seasoning performed after wet cleaning.

DETAILED DESCRIPTION OF THE PREFERRED EMBODIMENTS

Figure 1:
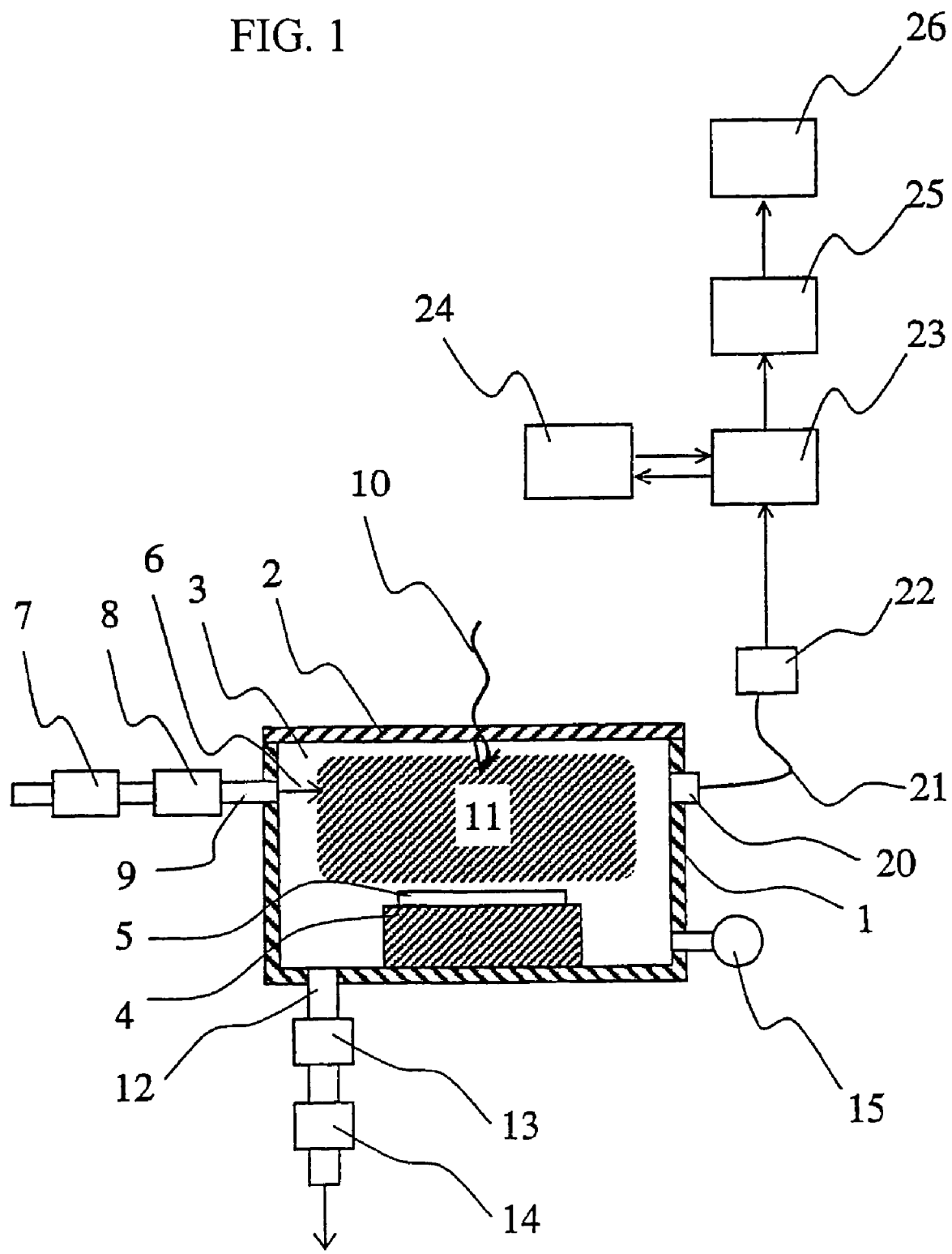
FIG. 1 is a cross-sectional view of a plasma etching apparatus according to a first embodiment of the invention.
Figure 2:
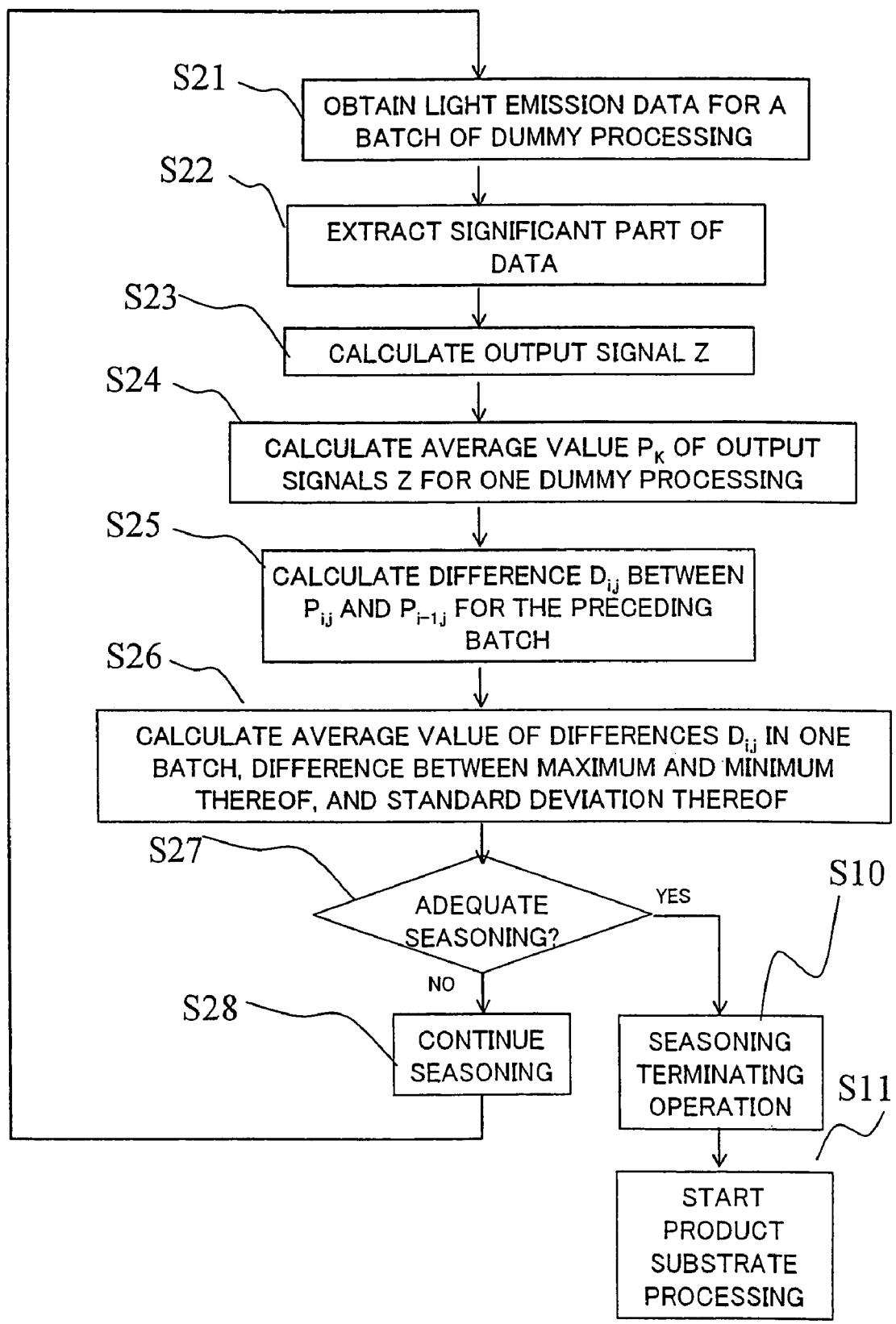
FIG. 2 is a flowchart showing a method for processing plasma emission data according to the first embodiment of the invention.

With reference to FIGS. 1 and 2, a first embodiment of the invention will be described in detail below. According to the first embodiment, plasma emission data for a dummy processing in a seasoning is obtained, and a principal component analysis is used for multivariate analysis of the plasma emission data. A plasma process includes dummy processings of one batch of substrates, the batch of substrates comprising 25 substrates.

FIG. 1 shows an arrangement of a microwave ECR (electron cyclotron resonance) plasma etching apparatus according to the first embodiment of the invention.

The microwave ECR plasma etching apparatus comprises a process chamber 3 having a process chamber wall 1 and a process chamber lid 2, a substrate holder 4, a process gas intake tube valve 7, a mass flow controller 8, a process gas intake tube 9, an exhaust port 12, a variable valve 13, an exhaust tube valve 14, a pressure gauge 15, a light-receiving part 20, an optical fiber 21, a spectrometer unit 22, an arithmetic unit 23, a database 24, a determination unit 25 and an apparatus control unit 26.

The process chamber lid 2 is mounted over the process chamber wall 1 to provide the process chamber 3. In the process chamber 3, the substrate holder 4 is installed, and a semiconductor substrate (object to be processed) 5 is mounted on the substrate holder 4.

The process gas 6 used for plasma etching is introduced into the process chamber 3 through the process gas intake tube valve 7, the mass flow controller 8 that adjusts the flow rate of the process gas 6, and the process gas intake tube 9. A microwave 10 transmitted from a microwave transmitter (not shown) is introduced into the process chamber 3, and the microwave 10 interacts with a magnetic field produced by a coil (not shown) to produce a plasma 11. The process gas 6 and a volatile material resulting from a reaction occurring during etching are discharged via the exhaust port 12. The exhaust port 12 is connected to a vacuum pump (not shown), which decompress the process chamber 3. The variable valve 13 and the exhaust tube valve 14 are connected between the exhaust port 12 and the vacuum pump (not shown). The variable valve 13 enables the pressure in the process chamber 3 during plasma etching to be adjusted. Opening and closing the exhaust tube valve 14 can switch between activation and inactivation of evacuation of the process chamber 3. The pressure in the process chamber 3 is measured with the pressure gauge 15 attached to the process chamber wall 1.

The light-receiving part 20 that enables reception of light emission of the plasma 11 is provided in the process chamber wall 1. The plasma emission received at the light-receiving part 20 is guided to the spectrometer unit 22 via the optical fiber 21. The plasma light is split into spectra by the spectrometer unit 22, and converted by CCDs (charge-coupled devices) in the spectrometer unit 22 into a multi-channel signal (a 1024-channel signal within a wavelength range from 200 nm to 800 nm, for example) regularly at predetermined sampling intervals (1 second, for example).

The multi-channel signal is input to the arithmetic unit 23. The arithmetic unit 23 can convert the multi-channel signal input from the spectrometer unit 22 into a number of signals. For example, it is assumed that the signal from the spectrometer unit 22 has n channels (1024 channels, for example), and these channels are collectively represented by one input signal vector s: s={s1, s2, . . . , sn}. Here, it is also assumed that a filter vector f, which represents a signal filter, is represented by f={f1, f2, . . . , fn}. Then, the arithmetic unit 23 calculates an inner product of the input signal vector s and the filter vector f using the following formula 1, thereby providing an output signal z.

$$Z = \sum_{i=1}^{n}(S_i \cdot f_i) \qquad \text{[Formula 1]}$$

The database 24 can store the filter vector f and transmit the filter vector f to the arithmetic unit 23 when the arithmetic unit 23 is to calculate the output signal z.

Now, a method for creating the signal filter will be described. While the arithmetic unit 23 may receive several input signals, it receives several hundreds to several thousands of input signals in the case where it takes the above-described light emission spectrum or the like as input. Therefore, a multivariate analysis is effectively used to create the signal filter. In this embodiment, a principal component analysis, which is one of multivariate analyses, is used. The principal component analysis is a common statistical processing and a specific example thereof is described in the following Non-patent Reference 1.

[Non-patent Reference 1]

Multivariate Analysis, by Tadakazu Okuno et al., JUSE Press, Ltd. (1971).

M input signal vectors s each having n input signals arranged in the direction of row are arranged in the direction of column, resulting in a signal matrix with m rows and n columns as represented by the following formula 2.

$$S = \begin{Bmatrix} s_{11} & s_{12} & s_{13} & \ldots & s_{1n} \\ s_{21} & s_{22} & s_{23} & \ldots & s_{2n} \\ \vdots & \vdots & \vdots & & \vdots \\ s_{m1} & s_{m2} & s_{m3} & \ldots & s_{mn} \end{Bmatrix}$$ [Formula 2]

Next, a covariance matrix X or correlation matrix of the signal matrix S is created, and an eigenvalue analysis is performed on the matrix X, which is a symmetric matrix with n rows and n columns. Then, n eigenvalues $\{\lambda 1, \lambda 2, \ldots, \lambda n\}$, which are positive real numbers, and n eigenvectors $\{y1, y2, \ldots, yn\}$ corresponding to the respective eigenvalues are obtained. Here, the order of the eigenvalues of $\lambda 1, \lambda 2, \ldots, \lambda n$ are descending order.

Each of the eigenvectors y is a one-dimensional vector with n rows. The formula 1 is calculated using the eigenvector as the filter vector f described above, whereby the signal filter that converts n input signals into one apparatus state signal is provided.

The output signal z produced by the arithmetic unit 23 is subjected to a further arithmetic processing as described later, and the arithmetic result (output signal) is transmitted to the determination unit 25. The determination unit 25 can make a determination concerning control of the apparatus based on the arithmetic result (output signal) and produce an apparatus control signal that indicates whether a seasoning is to be continued or not. The apparatus control signal produced by the determination unit 25 is transmitted to the apparatus control unit 26.

The apparatus control unit 26 is for controlling the plasma etching apparatus. For example, if the apparatus control unit 26 receives an apparatus control signal ordering to perform the seasoning, it continues the seasoning, or if it receives an apparatus control signal ordering to terminate the seasoning, it terminates the seasoning.

Now, with reference to FIGS. 2 to 7 and 14, a process according to the first embodiment will be described specifically.

In FIG. 2, first, light emission data for dummy processings of one lot of substrates in a seasoning is obtained (step S21). As described above, this step is equivalent to the process in which the plasma emission received at the light-receiving part 20 is converted in the spectrometer unit 22 into a multi-channel signal at predetermined sampling intervals and the multi-channels signal is transmitted to the arithmetic unit 23. The plasma emission data composed of the multi-channel signal is stored in the database 24 until the dummy processings of one batch (lot, herein) of substrates, which are being performed, are completed.

Then, a significant part of numerical data representing the plasma emission is extracted (step S22). According to the principal component analysis, a remarkable variation is intrinsically extracted. Accordingly, if the principal component analysis is performed on a series of light emission data obtained from the appearance of the plasma to the disappearance thereof, remarkable variations of the plasma at the times when it appears and disappears are picked up. Besides, if the principal component analysis is performed on a series of light emission data obtained from the appearance of the plasma to the disappearance thereof, in the case where the processing sequence consists of a plurality of steps with different processing conditions, a remarkable variation of the plasma caused by the processing condition changing when shifting from one step to another is picked up. Such a remarkable variation of the plasma causes a small but important variation of the plasma which indicates a transition of the state of the inside of the process chamber to be obscured. In order to avoid this disadvantage, it is essential to perform the principal component analysis on the plasma emission data excluding the data obtained when the plasma appears and disappears and when the processing sequence shifts from one step to another.

Figure 3:
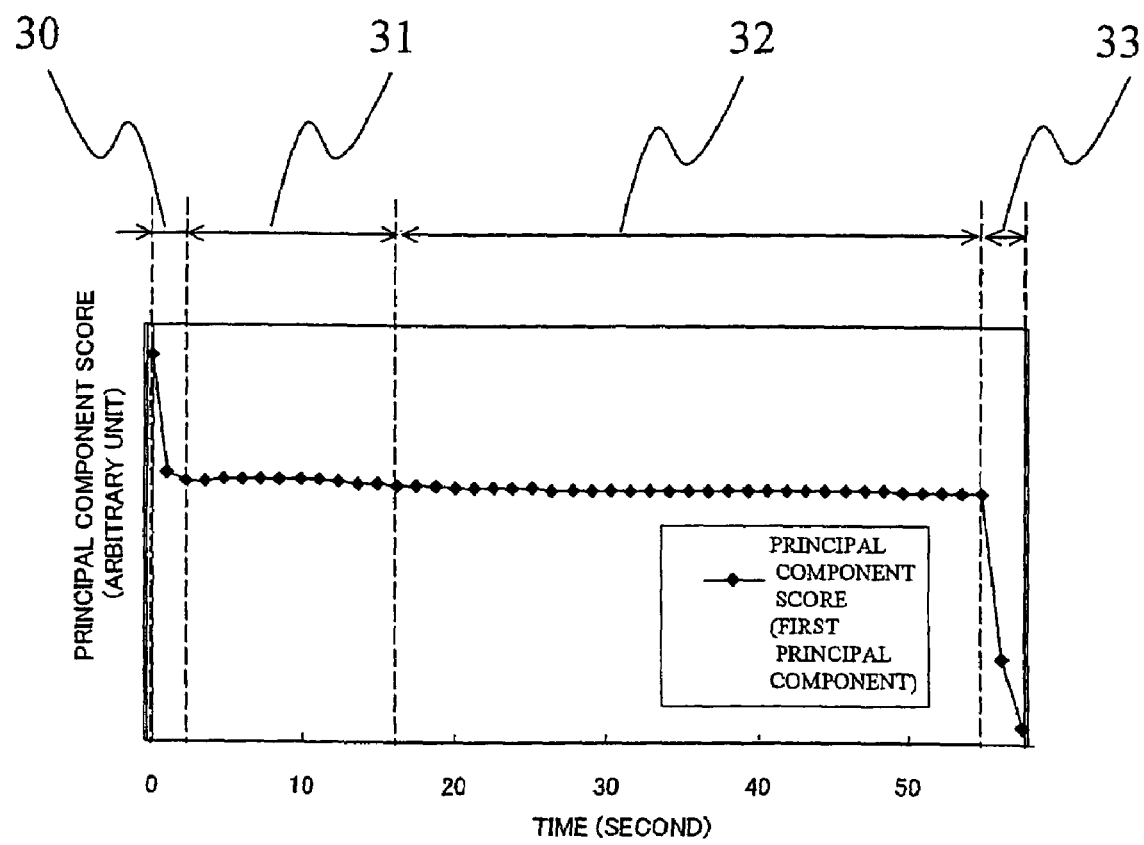
FIG. 3 is a graph showing a behavior of an output signal z (first principal component score) according to the first embodiment of the invention.
Figure 4:
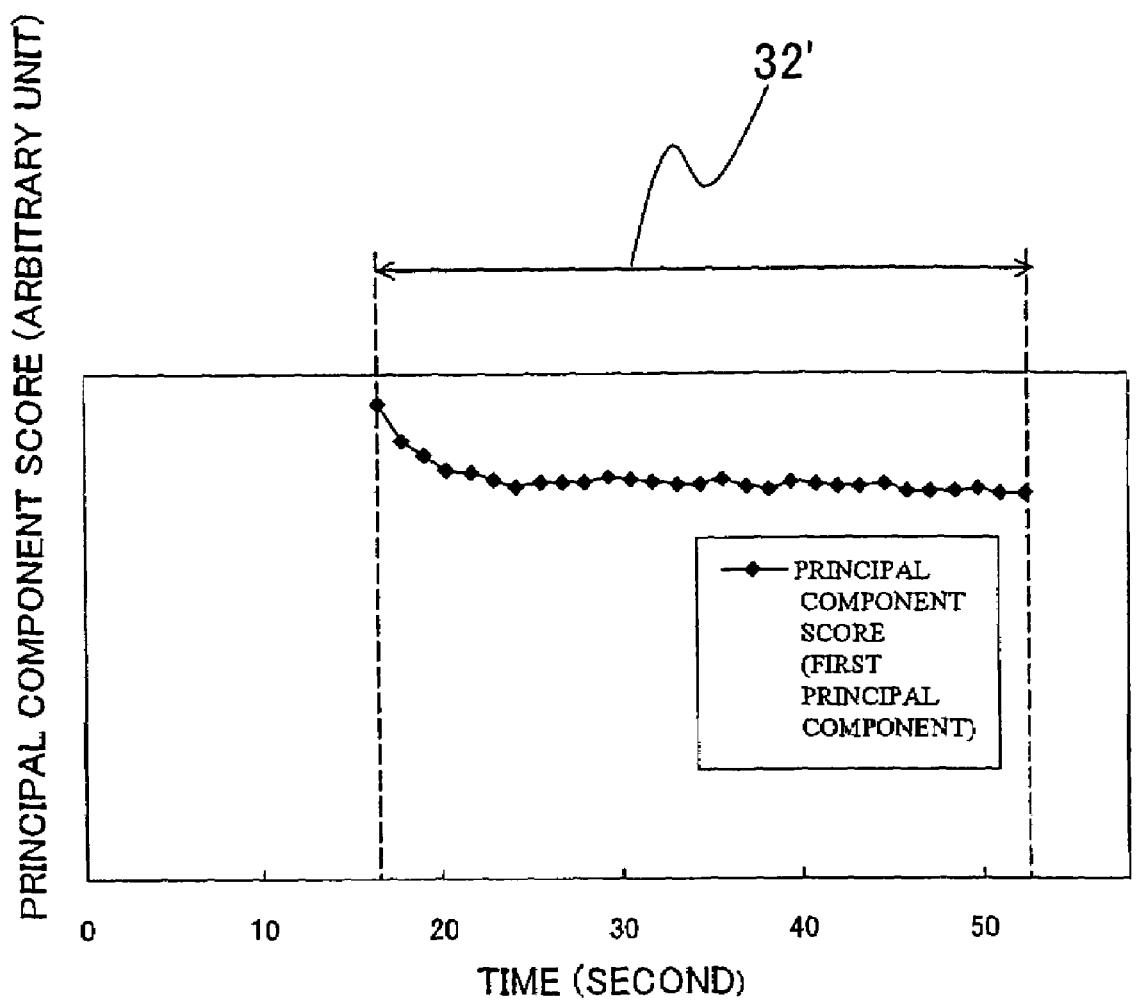
FIG. 4 is a graph showing a behavior of an output signal z (first principal component score) obtained from a significant part of the light emission data according to the first embodiment of the invention.

With reference to FIGS. 3 and 4, an operation S22 of extracting a significant part will be described specifically. FIG. 3 is a graph showing, for a plasma emission for a dummy processing of one dummy wafer, first principal component scores obtained by sampling the plasma emission at intervals of 1 second from the appearance to the disappearance of the plasma and performing the principal component analysis on the plasma emission data. In a region 30, there is shown a variation of the plasma caused by the appearance of the plasma and the succeeding unstable state thereof. In regions 31 and 32, there are shown variations of the plasma in first and second steps of the dummy processing, respectively. In a region 33, there is shown a variation of the plasma caused by the disappearance of the plasma. As can be seen, substantially no variation of the plasma is shown in the first and second steps in the graph of FIG. 3.

FIG. 4 is a graph showing first principal component scores obtained by performing the principal component analysis on the plasma emission data obtained from 17 seconds after the appearance of the plasma to 52 seconds after that. A region 32' is equivalent to the second step in the dummy processing. As can be seen from FIG. 4, a variation of the plasma in the second step can be grasped. Thus, a slight variation of the condition of the inside of the process chamber can be grasped. Ranges of the significant part used for the principal component analysis, that is, from what point in time to what point in time after the appearance of the plasma, or from what number of data sampling to what number of data sampling after the appearance of the plasma, are previously registered with the database 24. When the arithmetic unit 23 performs the principal component analysis, the range of the significant part of the plasma emission data is specified.

The dummy processing in the seasoning is repeatedly performed in the same processing sequence. Therefore, if a significant part of the plasma emission data is previously specified and registered with the database 24, the same significant part can be used for the following dummy processings.

While the second step of the dummy processing is used as the significant part of the plasma emission data herein, the plasma emission data is not limited thereto. For example, the first step of the dummy processing may be used as the significant part of the plasma emission data.

Next, the principal component analysis is performed on the significant part of the plasma emission data to calculate the output signal z (step S23). A first principal component score obtained by the principal component analysis constitutes the output signal z.

Next, an average value of the first principal component scores in one dummy processing calculated by the principal component analysis in the calculation step S23 is calculated (step S24). As shown in FIG. 4, the principal component scores are data obtained at certain sampling intervals (1 second, herein). For each of the dummy processings, the average value of the first principal component scores is calculated. In a k-th dummy processing, provided that a first principal component score for an i-th sampling is $a_i$, and the significant range of the plasma emission data for the dummy processing contains N sampled first principal component scores $a_i$, an average value $P_k$ of the first principal component scores for the k-th dummy processing is represented by the following formula 3.

$$P_k = \frac{\sum_{i=1}^{N} a_i}{N} \qquad \text{[Formula 3]}$$

Figure 5:
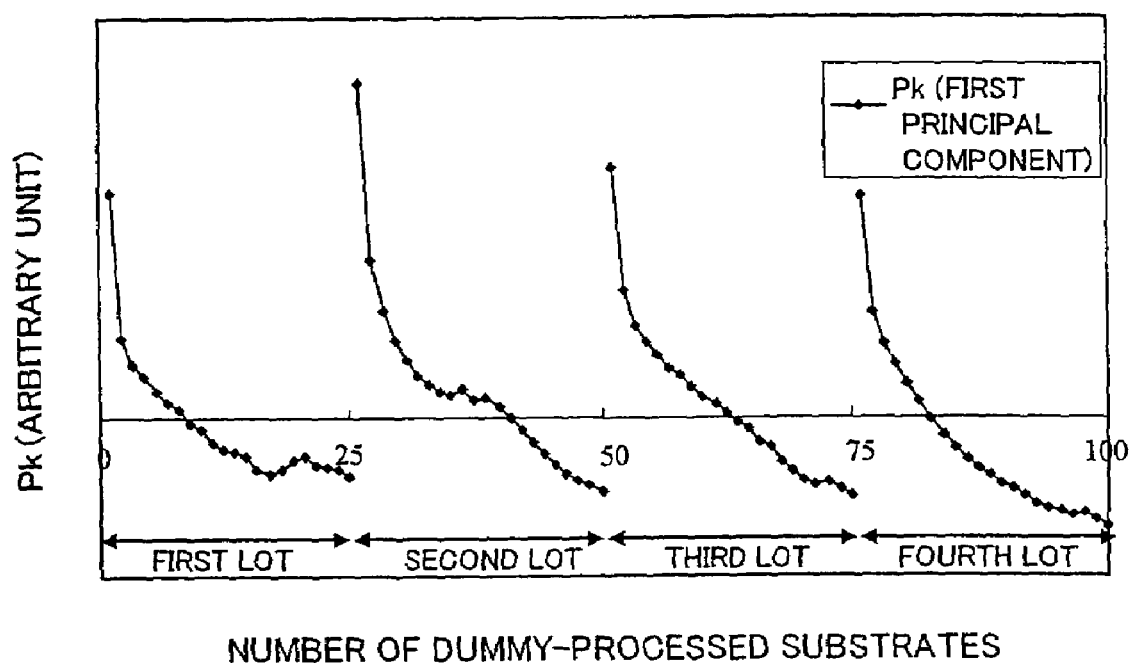
FIG. 5 is a graph showing a behavior of an average value of output signals z (first principal component scores) obtained from a significant region of the light emission data for each dummy processing according to the first embodiment of the invention.

FIG. 5 shows variations of the average value $P_k$ of the first principal component scores for the k-th dummy processing, the dummy processing being performed on four lots of substrates, one lot consisting of 25 substrates. FIG. 5 shows that the condition in the process chamber 3 is changed by the seasoning. However, this does not enable detection of the end point of the seasoning.

Next, in terms of the average value $P_k$ of the first principal component scores for each dummy processing, a difference between the first principal component score of a lot of interest and the first principal component score of the preceding lot is calculated (step S25). Provided that the average value P of the first principal component scores for a dummy processing of a j-th substrate in an i-th lot is $P_{i,j}$, the difference $D_{i,j}$ between the first principal component score $P_{i,j}$ for the dummy processing of the j-th substrate in the i-th lot and the first principal component score $P_{i-1,j}$ for the dummy processing of the j-th substrate in the (i−1)-th lot is represented by the following formula 4.

$$D_{i,j} = P_{i,j} - P_{i-1,j} \qquad \text{[Formula 4]}$$

If the condition in the process chamber is brought close to the stable condition during mass production by the seasoning, the dummy processings for the lots are performed with high repeatability. Therefore, the difference $D_{i,j}$ between the first principal component score $P_{i,j}$ for the lot for which the dummy processing has been finished and the first principal component score $P_{i-1,j}$ for the preceding lot enables evaluation of the inter-lot repeatability of the dummy processing, and thus, determination whether the seasoning is adequate or not, that is, determination of the end point of the seasoning.

Figure 6:
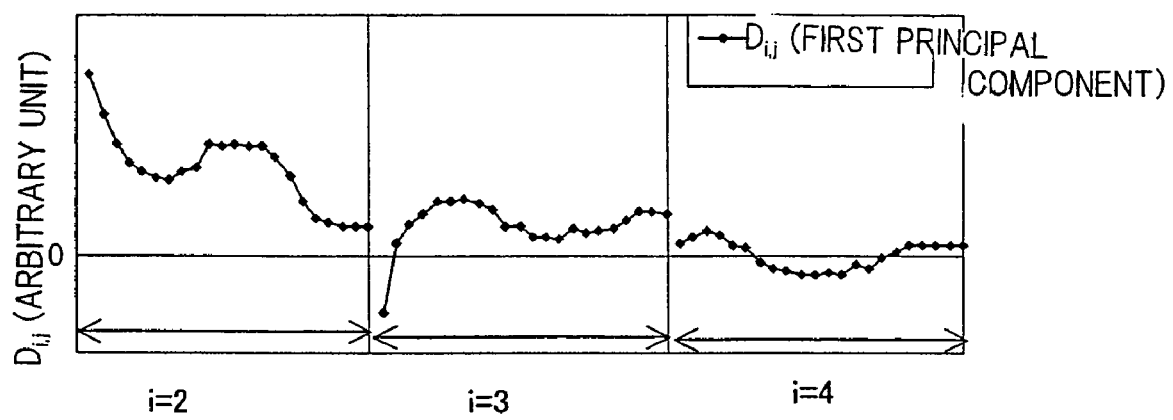
FIG. 6 shows a behavior of a difference $D_{i,j}$, between lots, of an average value $P_k$ of the output signals z (first principal component scores) obtained in each dummy processing according to the first embodiment of the invention.

FIG. 6 is a graph showing a behavior of the difference $D_{i,j}$. As can be seen from FIG. 6, as the dummy processing proceeds from one lot to the next lot, the value of $D_{i,j}$ totally decreases, and variations of the value in one lot also decreases.

Here, this step S25 of calculating the difference $D_{i,j}$ is omitted in the dummy processing of the first lot of substrates.

Next, the average value of the difference $D_{i,j}$ in one lot, the difference between the maximum and minimum of the difference $D_{i,j}$ in one lot, and the standard deviation of difference $D_{i,j}$ in one lot are calculated (step S26). The behavior of difference $D_{i,j}$ which totally decreases as the dummy processing proceeds from one lot to the next lot can be evaluated in terms of the average value AVE of the differences $D_{i,j}$ for one lot involving n dummy processings, which is represented by the following formula 5. In the formula 5, a subscript i of AVE indicates that the value AVE is an average value of the differences $D_{i,j}$ for the i-th lot.

$$AVE_i = \frac{\sum_{j=1}^{n} D_{i,j}}{n} \qquad \text{[Formula 5]}$$

Furthermore, the variation of the difference $D_{i,j}$ in one lot shown in FIG. 6 can be evaluated in terms of the difference $MAXMIN_i$ between the maximum and minimum of the differences $D_{i,j}$ in the i-th lot represented by the following formula 6 and the standard deviation $\sigma_i$ of the differences $D_{i,j}$ for the i-th lot represented by the following formula 7.

$$MAXMIN_i = (\text{maximum of } D_{i,j} \text{ for } i\text{-th lot}) - (\text{minimum of } D_{i,j} \text{ for } i\text{-th lot}) \qquad \text{[Formula 6]}$$

$$\sigma_i = \sqrt{\frac{\sum_{j=1}^{n}(D_{i,j} - AVE_i)^2}{n}} \qquad \text{[Formula 7]}$$

Next, it is determined whether the seasoning is adequate or not (step S27).

FIG. 7(a) is a graph showing an average value $AVE_i$ of the differences $D_{i,j}$ in one lot. FIG. 7(b) is a graph showing a difference $MAXMIN_i$ between the maximum and minimum of the differences $D_{i,j}$ in one lot. FIG. 7(c) is a graph showing a standard deviation $\sigma_i$ of the differences $D_{i,j}$ in one lot. These drawings show that the values decrease as the seasoning proceeds. This shows that since the condition in the process chamber 3 that has been changed by the wet cleaning S1 is brought close to the stable condition during mass production by the seasoning, the inter-lot repeatability of the plasma processing in the dummy processing is improved, and therefore, the value $D_{i,j}$ of the first principal component score reflecting the fact decreases as the seasoning proceeds.

If the values $AVE_i$, $MAXMIN_i$ and $\sigma_i$, which are calculated based on the first principal component score, are equal to or less than a preset threshold, it can be determined that the condition in the process chamber is bought close to the stable condition during mass production, that is, the seasoning reaches the end point.

For example, in this embodiment, the end point is determined to be reached because the value $AVE_i$ is equal to or less than a preset threshold 40, the value $MAXMIN_i$ is equal to or less than a preset threshold 42, and the value $\sigma_i$ is equal to or less than a preset threshold 44.

The values $AVE_i$, $MAXMIN_i$ and $\sigma_i$ shown in FIG. 7 are less than their respective thresholds when i=4. Therefore, it can be determined that the seasoning has reached the end point in the dummy processing for the fourth lot, that is, an adequate seasoning is attained in the dummy processing for the fourth lot.

Here, of the three values $AVE_i$, $MAXMIN_i$ and $\sigma_i$, the value $AVE_i$ can be negative. If the value $AVE_i$ is negative, the absolute value thereof decreases as the seasoning proceeds. Therefore, if the absolute value of the value $AVE_i$ is equal to or less than a preset threshold, it can be determined that the condition in the process chamber is brought close to the stable condition during mass production, that is, the seasoning reaches the end point.

In this first embodiment, because all the three values $AVE_i$, $MAXMIN_i$ and $\sigma_i$, are less than their respective thresholds when i=4, it is determined that the seasoning has reached the end point in the dummy processing for the fourth lot. However, it is not necessarily determined that the seasoning has reached the end point, even if all the three values are less than their respective thresholds. For example, it may be determined that the seasoning has reached the end point when one of the values $AVE_i$, $MAXMIN_i$ and $\sigma_i$ is less than the threshold. Alternatively, it may be determined that the seasoning has reached the end point when two of the values $AVE_i$, $MAXMIN_i$ and $\sigma_i$ are less than the threshold. Those who implement this invention can arbitrarily choose one of these.

Next, if it is determined that the seasoning is adequate in the determination step S27, an operation for terminating the seasoning is carried out (step S10). In this operation, a signal indicating to terminate the seasoning is transmitted from the determination unit 25 shown in FIG. 1 to the apparatus control unit 26, and the operation S10 of terminating the seasoning is carried out to enable start S11 of the product substrate processing. The operator may be informed of the termination of the seasoning.

On the other hand, if it is determined that the seasoning is inadequate in the determination step S27, a signal indicating to continue the seasoning is transmitted from the determination unit 25 shown in FIG. 1 to the apparatus control unit 26, and the seasoning is continued (step S28).

In this case, the process continues back to the step S21, light emission data for dummy processings of one lot of substrates is obtained.

By performing the above-described sequence, it can be determined whether the seasoning is adequate or not without the operator manually performing the confirmation processing S9. In addition, since the seasoning with a minimum number of dummy processings can be performed, the number of dummy substrates used can be reduced, and the availability of the plasma processing apparatus can be enhanced.

In the determination of the end point of the seasoning according to the first embodiment, the difference $D_{i,j}$ between the first principal component score $P_{i,j}$ for the dummy processing of the j-th substrate in the i-th lot and the first principal component score $P_{i-1,j}$ for the dummy processing of the j-th substrate in the (i-1)-th lot is used. In other words, the difference between the output signals z derived from the light emission data obtained in successive sequences of plasma processing for successive lots is used. Therefore, the precision of detection of the end point of the seasoning is less affected by a variation of the quality of the wet cleaning S1.

In the first embodiment, the principal component analysis is performed on the light emissions produced by the dummy processings in the seasoning which is being performed to calculate the filter vector f, thereby calculating the output signal z in the step S23. However, this invention is not limited thereto. The output signal z maybe calculated based on the formula 1 using the input signal vector s derived from the light emission produced by the dummy processing and a preset filter vector f.

The filter vector f used in this case may be the same as that obtained by the principal component analysis performed on the light emissions produced by the dummy processings in the seasoning immediately after the preceding wet cleaning. Alternatively, the filter vector f may be used which is obtained by the principal component analysis performed on the dummy light emissions in the seasoning immediately after the second or third previous wet cleaning, instead of the preceding wet cleaning. Alternatively, the filter vector f may be set in advance by a manufacturer of the plasma processing apparatus.

Furthermore, in the first embodiment, one lot of substrates, which are subjected to the dummy processing in batch, is equivalent to 25 substrates. However, this invention is not limited thereto. Even in the case where one lot of wafers consists of 25 wafers, if the dry cleaning is performed every 5 dummy processings in the seasoning, for example, that is, if the dummy processings S8-2 to S8-2" or dummy processings SB-3 to S8-3" consists of five dummy processings, the dummy processings are performed in batches of 5. In such a case, the process from the step S21 of obtaining the light emission data for dummy processings to the step S27 of determining whether the seasoning is adequate or not is performed in batches of 5 dummy processings.

Furthermore, even in the case where a short dry cleaning which is performed after each etching is performed after each of the dummy processings S8-2 to S8-2", if the dummy processings S8-3 to S8-3" consist of 5 dummy processings, the dummy processings are performed in batches of 5. In such a case, the process from the step S21 of obtaining the light emission data for dummy processings to the step S27 of determining whether the seasoning is adequate or not is performed in batches of 5 dummy processings.

Furthermore, in the first embodiment, the output signal Z is calculated by the principal component analysis in the calculation step S23, and only the first principal component score is used as the output signal z. However, this invention is not limited thereto. A plurality of principal component scores may be used as output signals z.

Figure 9:
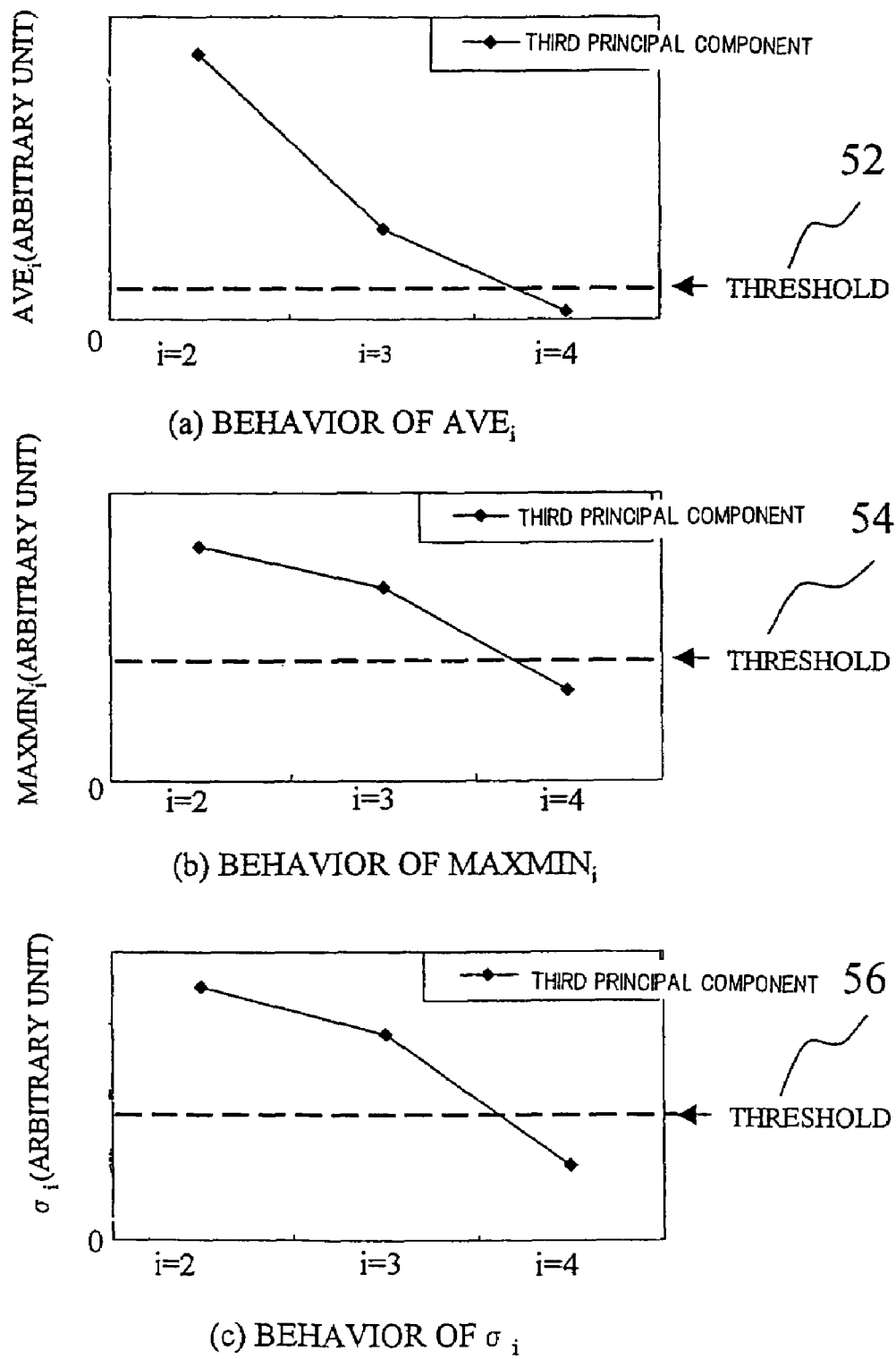
FIG. 9(a) is a graph showing a behavior of a value AVE$_i$ calculated based on the output signal z (third principal component score, here) according to the second embodiment.
FIG. 9(b) is a graph showing a behavior of a value MAXMIN$_i$ calculated based on the output signal z (third principal component score, here) according to the second embodiment.
FIG. 9(c) is a graph showing a behavior of a value σ$_i$ calculated based on the output signal z (third principal component score, here) according to the second embodiment.
Figure 10:
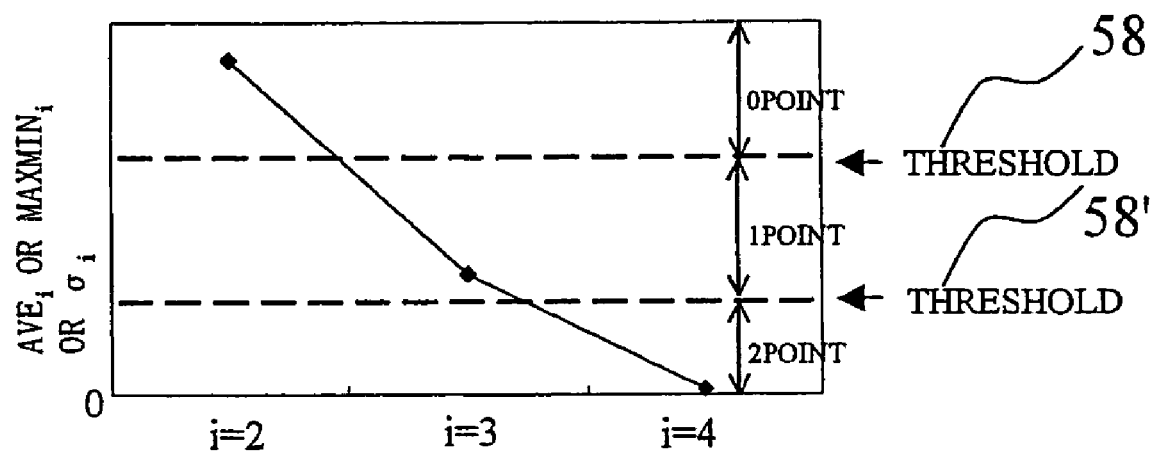
FIG. 10 illustrates a method of assigning a point to the values AVE$_i$, MAXMIN$_i$ and σ$_i$ calculated based on the output signal z according to the second embodiment.

Now, a second embodiment of the invention will be described with reference to FIGS. 8 to 11. While only the first principal component score is used as the output signal z in the first embodiment, second and third principal component scores are also used in this embodiment. In the principal component analysis, since a higher order principal component has more noise component, which leads to a reduction of validity of monitoring the condition in the process chamber, the principal components up to the third one are used in this embodiment. FIG. 8(a) shows an average value $AVE_i$ obtained using the second principal component score in the same manner as in the first embodiment. FIG. 8(b) shows a difference $MAXMIN_i$ based on the second principal component score. FIG. 8(c) shows a standard deviation a based on the second principal component score. Furthermore, FIG. 9(a) shows an average value $AVE_i$ obtained using the third principal component score in the same manner as in the first embodiment. FIG. 9(b) shows a difference $MAXMIN_i$ based on the third principal component score. FIG. 9(c) shows a standard deviation $\sigma_i$ based on the third principal component score. As can be seen, as is the case with the values $AVE_i$, $MAXMIN_i$ and $\sigma_i$ based on the first principal component score shown in FIG. 7, these values decrease as the seasoning proceeds. These values are compared with the preset thresholds, and if the values are equal to or less than the thresholds, it can be determined that the condition in the process chamber is bought close to the stable condition during mass production, that is, the seasoning reaches the endpoint.

Here, the threshold 40 set for the value $AVE_i$ based on the first principal component, the threshold 42 set for the value MAXMIN$_i$ based on the first principal component and the threshold 44 set for the value σ$_i$ based on the first principal component are not necessarily the same as the threshold 46 set for the value AVE$_i$ based on the second principal component, the threshold 48 set for the value MAXMIN$_i$ based on the second principal component and the threshold 50 set for the value σ$_i$ based on the second principal component, respectively, or the threshold 52 set for the value AVE$_i$ based on the third principal component, the threshold 54 set for the value MAXMIN$_i$ based on the third principal component and the threshold 56 set for the value σ$_i$ based on the third principal component, respectively. It is desirable that suitable thresholds are set for the values.

It may be determined that the seasoning is adequate when all the values AVE$_i$, MAXMIN$_i$ and σ$_i$ based on the first principal component, second principal component and third principal component are less than the preset thresholds. However, this invention is not limited thereto. For example, as shown in the graph in FIG. 10, two thresholds 58 and 58' may be set. If the value AVE$_i$, MAXMIN$_i$ or σ$_i$ is equal to or more than the threshold 58, the value is assigned a 0-point. If the value AVE$_i$, MAXMIN$_i$ or σ$_i$ is less than the threshold 58 and equal to or more than the threshold 58', the value is assigned an 1-point. If the value AVE$_i$, MAXMIN$_i$ or σ$_i$ is less than the threshold 58', the value is assigned a 2-point. Then, as shown in the table in FIG. 11, if the total point is more than a preset threshold (12, for example), it can be determined that the seasoning is adequate.

In this second embodiment, when i=2, the total point 60 is 1, when i=3, the total point 61 is 4, and when i=4, the total point 62 is 17. The total point is higher than the preset threshold (12, herein) when i=4. Thus, it can be determined that the seasoning reaches the end point during the fourth lot.

As described above with reference to this second embodiment, the precision of determination whether the seasoning is adequate or not can be improved by using the values AVE$_i$, MAXMIN$_i$ and σ$_i$ derived from a plurality of output signals z.

While the thresholds set in the second embodiment are numeric values, this invention is not limited thereto. The thresholds may be set in terms of percentage. For example, the threshold 58 may be set at 50 percent of the value AVE$_i$, MAXMIN$_i$ or σ$_i$ at the time when i=2 (setting percentage of 50%), the threshold 58' may be set at 20 percent of the value (setting percentage of 20%), and the succeeding values AVE$_i$, MAXMIN$_i$ and σ$_i$ may be assigned their respective points using these thresholds.

While in this second embodiment, two thresholds 58 and 58' are set for the values AVE$_i$, MAXMIN$_i$ and σ$_i$ derived from the first, second and third principal component scores, the number of the thresholds are not limited to two.

Furthermore, in this embodiment, the points, which are assigned to the values AVE$_i$, MAXMIN$_i$ and abased on the result of comparison of the values with their respective thresholds, are the same for the values (0-point, 1-point and 2-point, herein). However, this invention is not limited thereto. For example, if the significance of the values AVE$_i$, MAXMIN$_i$ and σ$_i$ derived from the second principal component score is higher than those derived from the other principal component scores, the values AVE$_i$, MAXMIN$_i$ and σ$_i$ derived from the second principal component score can be assigned larger points (0-point, 2-point and 4-point, for example). Similarly, of the values AVE$_i$, MAXMIN$_i$ and σ$_i$, the significance of the value AVE$_i$ is higher than the values MAXMIN$_i$ and σ$_i$, the value AVE$_i$ can be assigned a larger point (0-point, 2-point and 4-point, for example).

In this second embodiment, the first, second and third principal component scores are used as the output signals z. However, the number of the principal component scores used is not limited to three.

In this second embodiment, the principal component analysis is performed on the light emissions produced by the dummy processings in the seasoning which is being performed to calculate the filter vector f, thereby calculating the output signal z in the step S23. However, this invention is not limited thereto. A plurality of output signals z may be calculated based on the formula 1 using the input signal vector s derived from the light emission produced by the dummy processing and a plurality of preset filter vectors f.

The plurality of filter vectors f used in this case may be the same as those obtained by the principal component analysis performed on the light emissions produced by the dummy processings in the seasoning immediately after the preceding wet cleaning. Alternatively, a plurality of filter vectors f may be used which is obtained by the principal component analysis performed on the light emissions produced by the dummy processings in the seasoning immediately after the second or third previous wet cleaning, instead of the preceding wet cleaning. Alternatively, the filter vector f may be previously set by a manufacturer of a plasma processing apparatus.

Figure 12:
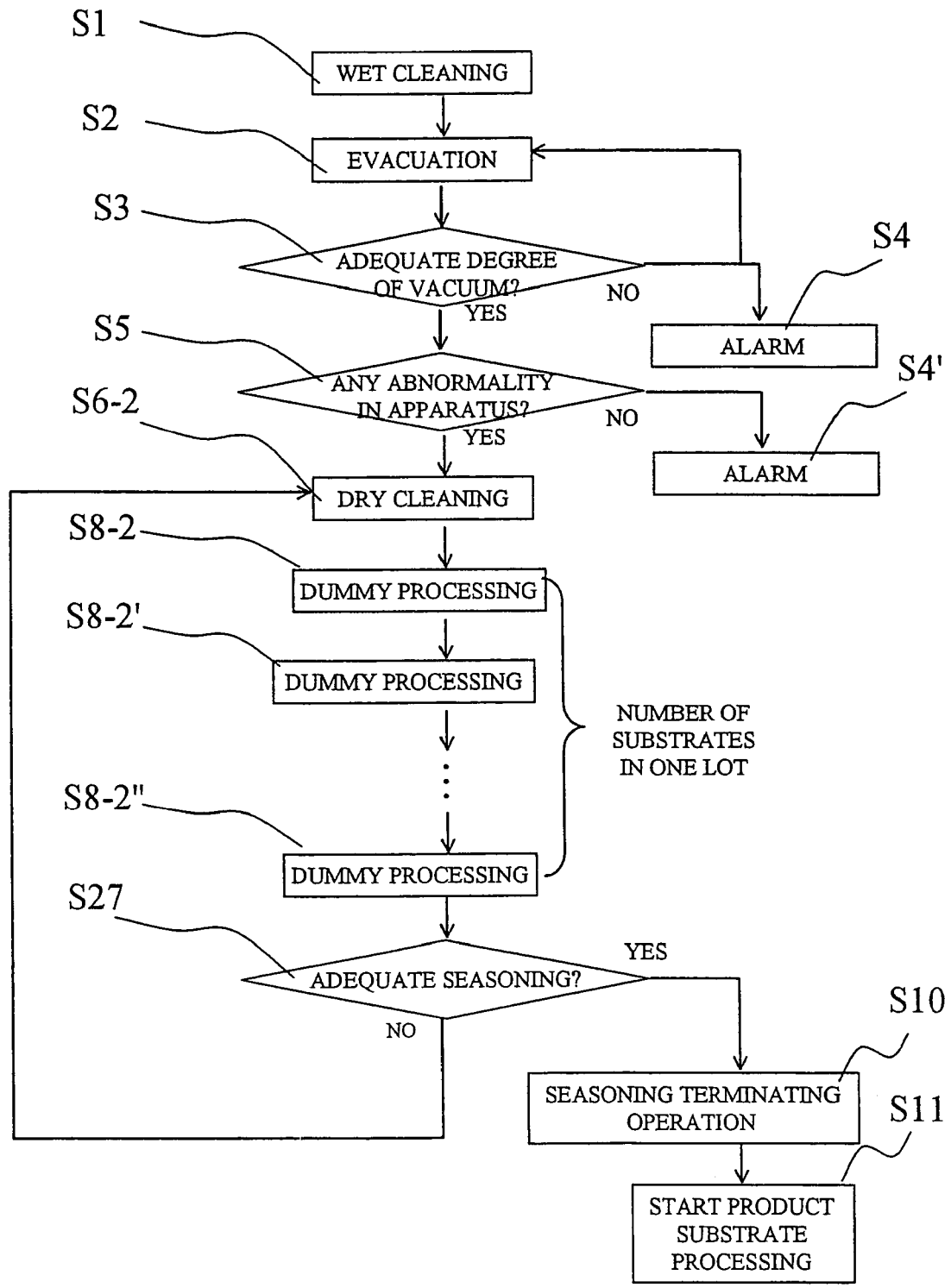
FIG. 12 is a flowchart illustrating a method in which evacuation of a process chamber, confirmation of the degree of vacuum, confirmation of an apparatus abnormality, and determination whether the seasoning is adequate or not, which are performed after wet cleaning, are all automatically performed.
Figure 13:
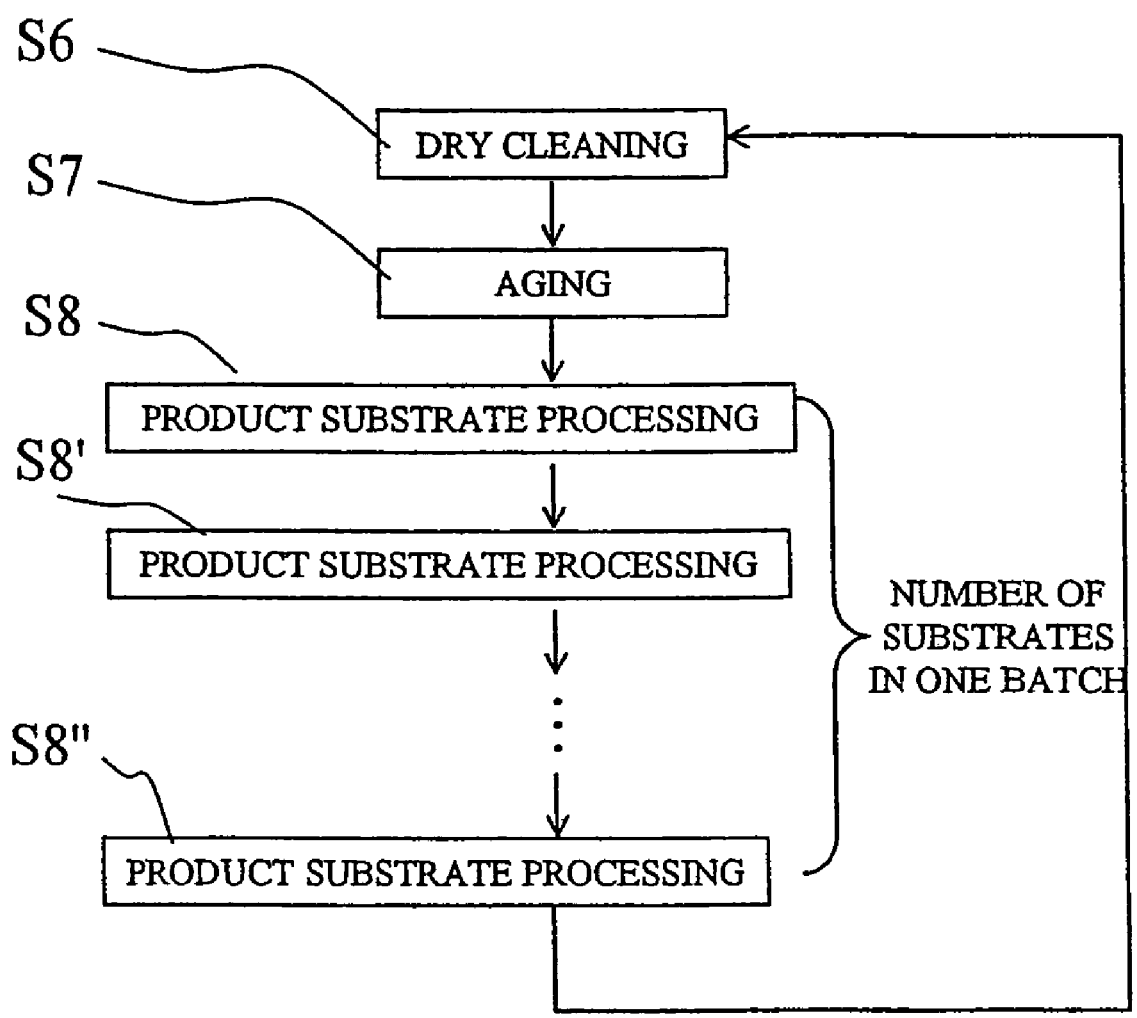
FIG. 13 is a flowchart of a common conventional product substrate processing.

Now, a third embodiment of the invention will be described with reference to FIGS. 1 and 12.

According to this third embodiment, the process from the start of the evacuation after the wet cleaning to the start of the product substrate processing S11 is carried out automatically, rather than manually by the operator, and a step of evacuation, a step of determining whether the degree of vacuum is adequate or not, and a step of determining whether there is an apparatus abnormality or not are added to the process described above.

First the plasma process chamber 3 is wet-cleaned (step S1).

Then, the process chamber lid 2 is closed, and then, the vacuum pump (not shown) connected to the exhaust port 10 is activated to start an operation S2 of evacuating the process chamber 3.

Then, an operation S3 of confirming whether a preset degree of vacuum is attained or not is automatically carried out. This operation is performed in such a manner that the pressure in the process chamber is measured automatically by means of the pressure gauge 15 attached to the process chamber 3. If the preset degree of vacuum is not attained, the evacuation is further continued. Furthermore, even after the evacuation operation S2 is performed for a preset period of time, if the preset degree of vacuum is not attained, an alarming operation S4 is automatically triggered. This operation may be provided by ringing a buzzer or providing an alarm indication on a monitor screen on the plasma processing apparatus, or, if the plasma processing apparatus is connected to a computer network, sending an electronic mail to a remote engineer or making a notification via a pager. In addition to giving the alarm, the vacuum pump (not shown) connected to the process chamber 3 may be stopped.

If it is confirmed that the preset degree of vacuum is attained in the confirmation operation S3, then, an operation S5 of confirming whether there is an apparatus abnormality or not is carried out automatically.

One example of the confirmation operation S5 is a leak check of the process chamber 3, that is, a confirmation of the amount of air introduced into the chamber per unit time. The amount L of air introduced into the process chamber 3 per unit time is calculated according to the following formula 8, where character T denotes a time during which the exhaust tube valve 14 is closed, character ΔP denotes an increase of the pressure in the process chamber 3 during the period in which the exhaust tube valve 14 is closed, and character v denotes a volume of the process chamber 3, in a state where the process gas intake tube valve 7, the mass flow controller 8 and the exhaust tube valve 14 are closed.

$$L = \frac{\Delta p \cdot V}{T} \qquad \text{[Formula 8]}$$

If the amount L of air introduced into the chamber per unit time, which is calculated based on the formula 8, is less than a preset threshold, the leak check is passed.

Another example of the confirmation operation S5 is a check of the mass flow controller 8 that adjusts the flow rate of the process gas introduced into the process chamber 3. This check involves adjusting the mass flow controller 8 to introduce a predetermined flow rate of process gas into the process chamber 3, and at the same time, detecting the increase of the pressure in the process chamber 3 caused by the introduction of the process gas 6 by means of the pressure gauge 15 attached to the process chamber 3, thereby confirming whether or not the mass flow controller 8 adequately introduces the predetermined flow rate of process gas into the process chamber 3. If the difference between the flow rate set in the mass flow controller 8 and the flow rate of the process gas 6 derived from the increase of the pressure in the process chamber 3 is less than a preset threshold, the check of the mass flow controller 8 is passed.

If the confirmation operation S5 proves that the plasma processing apparatus has an abnormality, an alarm is automatically given (step S4'). This step may be provided by ringing a buzzer or providing an alarm indication on a monitor screen on the plasma processing apparatus, or, if the plasma processing apparatus is connected to a computer network, sending an electronic mail to a remote engineer or making a notification via a pager. In addition to giving the alarm, the vacuum pump (not shown) connected to the process chamber 3 may be stopped.

If it is determined that the plasma processing apparatus has no abnormality in the confirmation operation S5, a dummy substrate, which is previously placed in the plasma processing apparatus, is automatically installed into the process chamber 3, and seasoning is automatically started. First, the dry cleaning S6-2 is performed, and then, the dummy processings S8-2 to S8-2" are performed. Plasma emissions produced in the dummy processings S8-2 to S8-2" are received at the light-receiving part 20, and an output signal z is calculated via the process described with reference to the first and second embodiments.

Then, the determination processing (step S27) of whether the seasoning is adequate or not is automatically performed via the process described with reference to the first and second embodiments.

If the dummy processings are those performed on the first batch of substrates, the determination processing S27 is omitted, and the process automatically continues to the dry cleaning S6-2.

If it is determined that the seasoning is inadequate in the determination processing S27, the process automatically moves on to the dry cleaning S6-2. On the other hand, if it is determined that the seasoning is adequate in the determination processing S27, the seasoning terminating operation S10 is performed. In this case, a signal indicating to terminate the seasoning is transmitted from the determination unit 25 shown in FIG. 1 to the apparatus control unit 26, and the seasoning terminating operation S10 is carried out to enable start S11 of the product substrate processing. In addition, the operator may be informed of the termination of the seasoning.

By performing the above-described sequence, preparation for the seasoning and the seasoning itself can be automatically performed after the evacuation following the wet cleaning, it can be automatically determined whether the seasoning is adequate or not, and preparation for stating the product substrate processing can be carried out. Therefore, it can be automatically determined whether the seasoning is adequate or not without the confirmation processing S9 by the operator, which would be required in the prior art. In addition, since the seasoning with a minimum number of dummy processings can be performed, the number of dummy substrates used can be reduced, and the time required for the seasoning can be reduced, whereby the throughput of the plasma processing apparatus can be enhanced.

While in the first to third embodiments, the plasma emission data used for determining the end point of the seasoning is obtained in the dummy processing, this invention is not limited thereto. For example, if a short dry cleaning which is performed after each etching is performed after each of the dummy processings, it can be determined whether the seasoning is adequate or not using the plasma emission obtained in the short dry cleaning performed after etch etching in the same manner as in the first to third embodiments.

While in the first to third embodiments, the principal component analysis is used as a method of multivariate analysis performed on the plasma emission produced in the plasma processing in the seasoning, this invention is not limited thereto.

While the plasma etching apparatus has been described regarding the first to third embodiment, the application of this invention is not limited to the plasma etching apparatus. This invention can be applied to other plasma processing apparatuses, such as a plasma CVD apparatus.

While the semiconductor substrate has been described regarding the first to third embodiments, the application of this invention is not limited to the semiconductor substrate. This invention can be applied to plasma processing of other substrates, such as a LCD substrate.

As described above, according to the invention, it can be determined whether the seasoning is adequate or not by splitting a plasma emission produced in a batch of plasma processings into spectra, performing a multivariate analysis on the light emission data to calculate output signals, finding the differences between the output signals and those obtained in the preceding batch of plasma processings, calculating the average value of the differences in one batch, the difference between the maximum and minimum values thereof in one batch, and the standard deviation thereof in one batch, and comparing these values with a preset threshold. Thus, there can be provided plasma processing apparatus and method that allow the number of substrates which are dummy-processed in the seasoning to be reduced.

What is claimed is:

1. A plasma processing method to subject substrates to plasma processing in lots having:
   a light-receiving part for monitoring a plasma emission in a process chamber;

a spectrometer unit for performing a spectrometry on said plasma emission and to convert the same into a multi-channel signal;

an arithmetic unit for performing principal component analysis on the multi-channel signal for each substrate to obtain an average of principal component scores ($P_{ij}$ for j-th substrate of i-th lot);

a database for storing a filter vector for obtaining the principal component scores;

and a controller for controlling an operation of said plasma processing apparatus; the method comprising:

step (A) of determining a difference ($D_{ij}=P_{ij}-P_{i-1,j}$) of average principal component scores of a substrate in a lot compared to that of a substrate in an identical position in the previous lot;

step (B) of determining an average, a difference of minimum and maximum, and a standard deviation of ($D_{ij}$) for all substrates in a lot; and step (C) of comparing the average, the difference of minimum and maximum, and the standard deviation, as determined, with preset thresholds to determine an end point of seasoning.

2. The plasma processing method according to claim 1, wherein the principal component scores include at least one of a first principal component, a second principal component, and a third principal component.

3. The plasma processing method according to claim 2, wherein the step (B) of determining effects the respective determinations based upon at least one of the first principal component, the second principal component and the third principal component.

4. The plasma processing method according to claim 3, wherein the step (B) effects the respective determinations for the first principal component.

5. The plasma processing method according to claim 3, wherein the step (B) effects the respective determinations for the second principal component.

6. The plasma processing method according to claim 3, wherein the step (B) effects the respective determinations for the third principal component.

7. The plasma processing method according to claim 1, further comprising:

a step of performing evacuation after a wet cleaning;

a step of automatically determining whether a degree of vacuum is adequate or not; and a step of automatically determining whether there is an apparatus abnormality or not.

8. The plasma processing method according to claim 7, wherein the principal component scores include at least one of a first principal component, a second principal component, and a third principal component.

9. The plasma processing method according to claim 8, wherein the step (B) of determining effects the respective determinations based upon at least one of the first principal component, the second principal component and the third principal component.

10. The plasma processing method according to claim 9, wherein the step (B) effects the respective determinations for the first principal component.

11. The plasma processing method according to claim 9, wherein the step (B) effects the respective determinations for the second principal component.

12. The plasma processing method according to claim 9, wherein the step (B) effects the respective determinations for the third principal component.

* * * * *